(12) United States Patent
Fowler

(10) Patent No.: US 10,813,843 B2
(45) Date of Patent: Oct. 27, 2020

(54) PERSONALIZED MEDICATION DISPENSER

(71) Applicant: Lester Fowler, Rotonda West, FL (US)

(72) Inventor: Lester Fowler, Rotonda West, FL (US)

( * ) Notice: Subject to any disclaimer, the term of this patent is extended or adjusted under 35 U.S.C. 154(b) by 0 days.

(21) Appl. No.: 16/241,709

(22) Filed: Jan. 7, 2019

(65) Prior Publication Data

US 2020/0214939 A1    Jul. 9, 2020

(51) Int. Cl.
| | | |
|---|---|---|
| *A61J 7/04* | (2006.01) | |
| *G16H 20/13* | (2018.01) | |
| *G16H 10/60* | (2018.01) | |
| *G07C 9/00* | (2020.01) | |

(52) U.S. Cl.
CPC ........... *A61J 7/0472* (2013.01); *A61J 7/0445* (2015.05); *G16H 20/13* (2018.01); *A61J 7/049* (2015.05); *A61J 7/0436* (2015.05); *A61J 2200/30* (2013.01); *G07C 9/00563* (2013.01); *G16H 10/60* (2018.01)

(58) Field of Classification Search
CPC ...... A61J 7/0472; A61J 7/0445; A61J 7/0436; A61J 2200/30; A61J 7/049; G16H 20/13; G16H 10/60; G07C 9/00563
USPC ................................................. 700/231–244
See application file for complete search history.

(56) References Cited

U.S. PATENT DOCUMENTS

| | | | | |
|---|---|---|---|---|
| 8,378,827 B2 * | 2/2013 | Davidowitz | ....... | G08B 13/2431 312/400 |
| 9,572,748 B2 * | 2/2017 | Lim | ................. | G07C 9/38 |
| 10,124,940 B2 * | 11/2018 | Blackburn | ............. | G16H 20/13 |
| 10,198,556 B2 * | 2/2019 | Herman | ................ | A61J 7/0454 |
| 10,543,323 B2 * | 1/2020 | Buchberger | .......... | A24F 47/008 |
| 10,675,216 B2 * | 6/2020 | Mejia | ........................ | A61J 7/04 |
| 2006/0071011 A1 * | 4/2006 | Varvarelis | ............. | A61J 7/0481 221/9 |
| 2008/0140250 A1 * | 6/2008 | Dave | ........................ | G07C 9/37 700/237 |
| 2010/0318218 A1 * | 12/2010 | Muncy, Jr. | .......... | G06F 19/3462 700/220 |

(Continued)

*Primary Examiner* — Michael Collins
(74) *Attorney, Agent, or Firm* — The Iwashko Law Firm, PLLC; Lev Ivan Gabriel Iwashko

(57) ABSTRACT

A personalized medication dispenser, including a main body to store medication therein, the main body including a first end having a base, and a second end having an aperture through which the medication is extracted and a cap to prevent the medication from being extracted from the aperture of the second end, the cap including a top portion, including a biometric scanner disposed on a surface of the top portion to scan biometric information of a user, a controller disposed within the top portion to determine whether the biometric information is from authorized user, and a medication receiving compartment disposed within the top portion to receive the medication in response to the determination that the scanned biometric information is from the authorized user, a bottom portion to be at least partially inserted within the aperture of the second end, and a manual slide disposed between the top portion and the bottom portion to slide to an open position in response to the determination that the scanned biometric information is from the authorized user, such that the medication is received in the medication receiving compartment when the manual slide is in the open position.

9 Claims, 2 Drawing Sheets

(56) References Cited

U.S. PATENT DOCUMENTS

| | | | |
|---|---|---|---|
| 2013/0200033 A1* | 8/2013 | Zonana | B65D 83/0409 |
| | | | 215/231 |
| 2014/0074283 A1* | 3/2014 | Blackburn | A61J 7/0076 |
| | | | 700/237 |
| 2014/0214200 A1* | 7/2014 | Chrusciel | G06F 19/3462 |
| | | | 700/237 |
| 2014/0238423 A1* | 8/2014 | Tucker | A24F 47/008 |
| | | | 131/328 |

* cited by examiner

PERSONALIZED MEDICATION DISPENSER

BACKGROUND

1. Field

The present general inventive concept relates generally to a medication dispenser, and particularly, to a personalized medication dispenser.

2. Description of the Related Art

Prescription drugs are easily obtained, allowing misuse to become increasingly widespread. Due to insufficient monitoring and regulation of distribution, drug abuse can cause physical and emotional pain for abusers as well as their families.

There are limited solutions on the market that limit the distribution of pills to a patient. The standard plastic bottles given to the patient can be used at their discretion, regardless of the doctor's instructions. Medication bottles typically have a screw-on cap. As such, these bottles provide inadequate protection from unauthorized users or allow authorized users unfettered access.

Therefore, there is a need for a tamper proof medication dispenser.

SUMMARY

The present general inventive concept provides a personalized medication dispenser.

Additional features and utilities of the present general inventive concept will be set forth in part in the description which follows and, in part, will be obvious from the description, or may be learned by practice of the general inventive concept.

The foregoing and/or other features and utilities of the present general inventive concept may be achieved by providing a personalized medication dispenser, including a main body to store medication therein, the main body including a first end having a base, and a second end having an aperture through which the medication is extracted and a cap to prevent the medication from being extracted from the aperture of the second end, the cap including a top portion, including a biometric scanner disposed on a surface of the top portion to scan biometric information of a user, a controller disposed within the top portion to determine whether the biometric information is from authorized user, and a medication receiving compartment disposed within the top portion to receive the medication in response to the determination that the scanned biometric information is from the authorized user, a bottom portion to be at least partially inserted within the aperture of the second end, and a manual slide disposed between the top portion and the bottom portion to slide to an open position in response to the determination that the scanned biometric information is from the authorized user, such that the medication is received in the medication receiving compartment when the manual slide is in the open position.

The biometric scanner may be at least one of a fingerprint scanner, an iris scanner, a facial scanner, and a voice scanner.

The manual slide may be unable to move prior to the determination that the scanned biometric information is from the authorized user.

The top portion may further include a sensor disposed within the top portion to detect the user has tampered with or attempted to tamper with at least one of the cap and the main body.

The top portion may further include a timer disposed within the top portion having at least one of a clock, an alarm, and a countdown functionality.

The personalized medication dispenser may further include a conductive tape disposed within the main body such that the controller instructs the timer to alert a third party, when the sensor detects the user has tampered with or attempted to tamper with the cap.

The personalized medication dispenser may further include a wire mesh disposed within the main body such that the controller instructs the timer to alert a third party, when the sensor detects the user has tampered with or attempted to tamper with the main body.

The top portion may further include a light disposed within the top portion to turn on when the alarm is triggered.

The controller may instruct the timer to turn on the light when the sensor detects the user has tampered with or attempted to tamper with the cap.

The controller may instruct the timer to turn on the light when the sensor detects the user has tampered with or attempted to tamper with the cap.

The controller may instruct the timer to alert a third party that the manual slide has remained in the open position for a predetermined amount of time in response to the manual slide remaining in the open position for a predetermined amount of time.

The third party may be at least one of a prescribing doctor, family, and police.

BRIEF DESCRIPTION OF THE DRAWINGS

These and/or other features and utilities of the present generally inventive concept will become apparent and more readily appreciated from the following description of the embodiments, taken in conjunction with the accompanying drawings of which.

DETAILED DESCRIPTION

Various example embodiments (a.k.a., exemplary embodiments) will now be described more fully with reference to the accompanying drawings in which some example embodiments are illustrated. In the figures, the thicknesses of lines, layers and/or regions may be exaggerated for clarity.

Accordingly, while example embodiments are capable of various modifications and alternative forms, embodiments thereof are shown by way of example in the figures and will herein be described in detail. It should be understood, however, that there is no intent to limit example embodiments to the particular forms disclosed, but on the contrary, example embodiments are to cover all modifications, equivalents, and alternatives falling within the scope of the disclosure. Like numbers refer to like/similar elements throughout the detailed description.

It is understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements and/or components, but do not preclude the presence or addition of one or more other features, integers, steps, operations, elements, components and/or groups thereof.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art. However, should the present disclosure give a specific meaning to a term deviating from a meaning commonly understood by one of ordinary skill, this meaning is to be taken into account in the specific context this definition is given herein.

Figure 1:
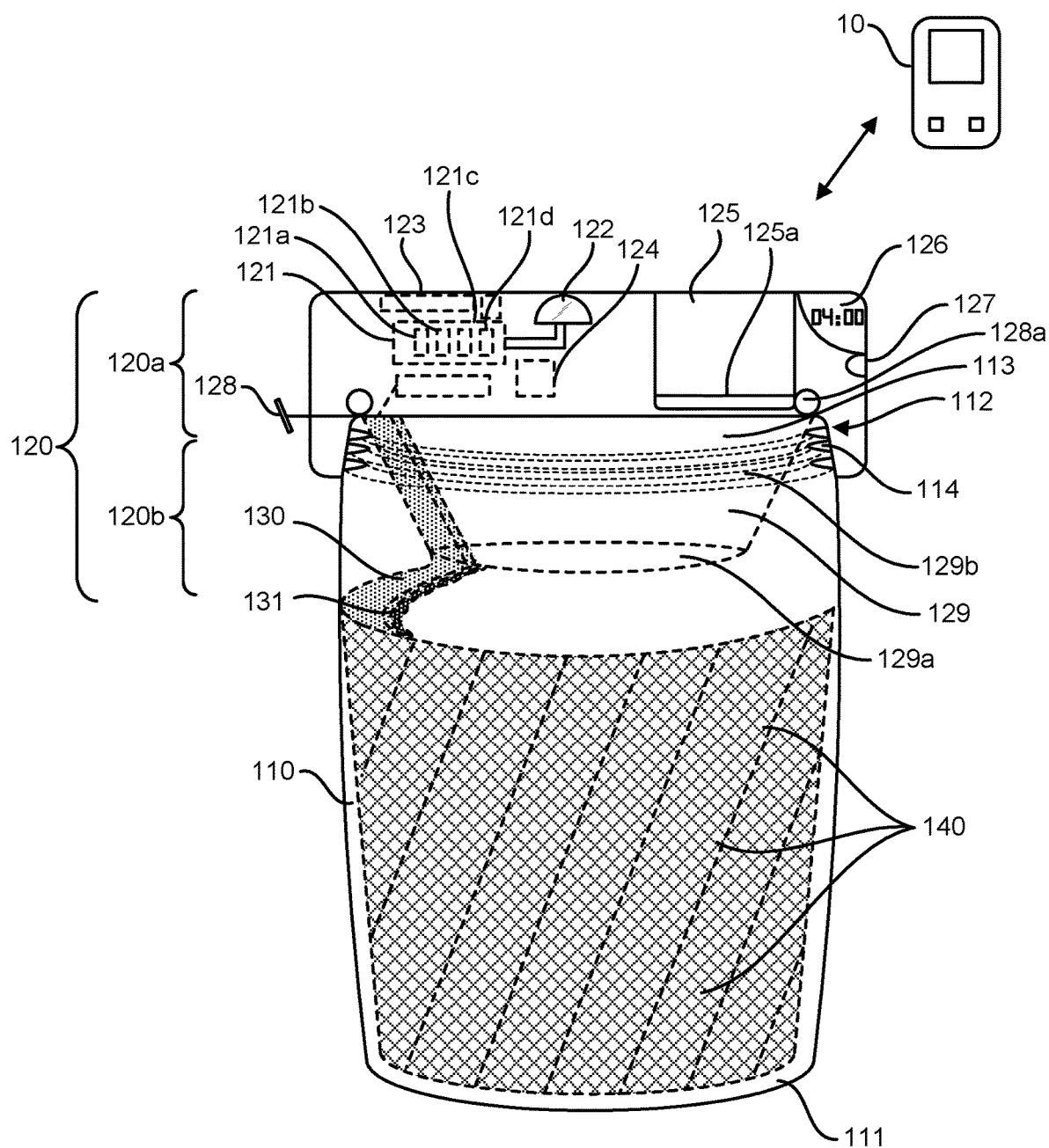
FIG. 1 illustrates a side view of a personalized medication dispenser, according to an exemplary embodiment of the present general inventive concept.

FIG. 1 illustrates a side view of a personalized medication dispenser 100, according to an exemplary embodiment of the present general inventive concept.

The personalized medication dispenser 100 may be constructed from at least one of plastic, metal, wood, stone, ceramic, rubber, closed-cell extruded polystyrene foam, etc., but is not limited thereto.

The personalized medication dispenser 100 may include a main body 110, a cap 120, a conductive tape 130, and a wire mesh 140, but is not limited thereto.

Referring to FIG. 1, the main body 110 is illustrated to have a cylindrical shape. However, the main body 110 may be rectangular, conical, spherical, or any shape known to one of ordinary skill in the art. The main body 110 may be of any predetermined size to contain, and store therein, medication of various sizes. Furthermore, the main body 110 may contain liquid or solid medications.

The main body 110 may include a first end 111, a second end 112, an aperture 113, and at least one threaded ridge 114, but is not limited thereto. The first end 111 may include a base, which may allow the main body 110 to stand on a surface. The second end 112 may have the aperture 113 to allow access to an inner portion of the main body 110. As such, medication may be deposited within the main body 110 or extracted from the main body 110 through the aperture 113.

The cap 120 may include a top portion 120a and a bottom portion 120b, but is not limited thereto.

The top portion 120a may include a controller 121, a biometric scanner 122, at least one battery 123, a recharge port 123a, a sensor 124, a medication receiving compartment 125, a door 125a, a timer 126, a light 127, a manual slide 128, and a lock 128a, but is not limited thereto.

The bottom portion 120b may include a funnel 129, a funnel aperture 129a, and at least one rib 129b, but is not limited thereto.

The controller 121, the at least one battery 123, the sensor 124, the medication receiving compartment 125, the door 125a, and the lock 128a may be disposed within and/or may be affixed and/or adhered to the inside of the top portion 120a, at any feasible location. The biometric scanner 122, the recharge port 123a, the timer 126, and the light 127 may be disposed on the exterior of the top portion 120a, at any feasible location. The manual slide 128 may be disposed between the top portion 120a and the bottom portion 120b. Furthermore, the manual slide 128 may have at least a portion disposed within an interior portion of the cap 120 and at least a portion protruding on an exterior portion of the cap 120.

The controller 121 may include a central processing unit (CPU) 121a, a memory 121b, a storage unit 121c, and a transceiver 121d, but is not limited thereto. The CPU 121a may perform all calculation and processing functions. The CPU 121a may interact with the memory 121b by running/executing programs and/or retrieving data from the storage unit 121c. The storage unit 121c may maintain a database and/or storage of a user's biometric information, whether the user is an authorized user, a time of when the user may access the medication as authorized, and any third party information, but is not limited thereto. The controller 121 may be physically and electrically connected to the biometric scanner 122, the at least one battery 123, the recharge port 123a, the sensor 124, the timer 126, the light 127, and the lock 128a. As such, the controller 121 may control and/or regulate all the functions of all the components within the cap 120. Additionally, the timer 126 may provide functionality, such as a clock, a countdown, and/or an alarm, but is not limited thereto.

The transceiver 121d may allow communication between the controller 121 and an external control unit 10, which may occur with a wired and/or wireless connection using BLUETOOTH, near-field communication (NFC), WIFI, satellite, RFID communication, etc., but is not limited thereto. As such, the transceiver 121d may allow the personalized medication dispenser 100 to be tracked via a GPS signal.

The external control unit 10 may be a device having wireless communication capabilities, including, but not limited to, a cellular telephone, a laptop computer, a desktop computer, a tablet computer, a PDA, a smart watch, etc. Furthermore, the external control unit 10 may control and/or regulate all the functions of all the components within the cap 120, and may allow the CPU 121a to be programmed to include information relating to the user and/or third party information.

Also, the external control unit 10 may display a map thereon to correspond to the GPS signal emitted by the transceiver 121d, in order to track and monitor a location of the personalized medication dispenser 100.

The biometric scanner 122 may include at least one of a fingerprint scanner, an iris scanner, a facial scanner, a voice scanner (collectively, biometric information), etc., but is not limited thereto. The storage unit 121c may be initialized with the user's biometric information via at least one of a third party entering data into the storage unit 121c using previously obtained biometric information or an initial biometric scan using the biometric scanner 122 upon the user obtaining the personalized medication dispenser 100, but is not limited thereto.

The at least one battery 123 may be lithium-ion, nickel cadmium, nickel metal hydride, alkaline, etc., but is not limited thereto. The recharge port 123a may connect to an external power source to recharge the at least one battery 123.

The funnel 129 may have a conical shaped appearance. Specifically, the shape of the funnel 129 may accommodate any predetermined sizes of the aperture 113 of the main body 110. Additionally, the at least one rib 129b may interlock with the at least one threaded ridge 114. In other words, the at least one rib 129b on the funnel 129, corresponds to the at least one threaded ridge 114 on the main body 110, such that when the bottom portion 120b is inserted into the main body 110 through the aperture 113, the user may twist the cap 120 in a clockwise direction with respect to a top view of the cap 120. As such, the twisting of the cap 120 may secure the cap 120 to the main body 110 by the at least one rib 129b becoming interwoven between the at least one threaded ridge 114. Furthermore, the at least one threaded ridge 114 may prevent children from removing the cap 120, thereby making the at least one threaded ridge 114, childproof.

The conductive tape 130 may be disposed near the second end 112 on the interior of the main body 110. The conductive tape 130 may include an adhesive 131. The adhesive 131 may affix and/or adhere the conductive tape 130 to a portion of the main body 110, at any point determined by the user. A pharmacist or any person creating an order for medication using the personalized medication dispenser 100 may affix and/or adhere the conductive tape 130 using the adhesive 131 inside the main body 110 prior to depositing the medication within the main body 110. The conductive tape 130 may be physically and electrically connected to the sensor 124 and the controller 121. The conductive tape 130 may be an electrical wire or a metallic contact point.

The wire mesh 140 may be disposed within the main body 110. Specifically, the wire mesh 140 may be disposed within the material, of which, the main body 110 is constructed therefrom or the wire mesh 140 may be an auxiliary addition, such that it is affixed and/or adhered to the interior of the main body 110. The wire mesh 140 may be physically and electrically connected to the sensor 124 and the controller 121.

The sensor 124 may use the conductive tape 130 and/or the wire mesh 140 to detect when the user is tampering or attempting to tamper with the main body 110, the manual slide 128, and/or the cap 120. Tampering or attempting to tamper may include the user's failure to touching the biometric scanner 122, before attempting to open the cap 120 or before attempting to pull the manual slide 128. Moreover, when the manual slide 128 has been pulled, it is considered in an open position. Simultaneously, the door 125a opens and the timer 126 may begin a countdown of a predetermined amount of time. As such, the controller 121 may determine the user is tampering or attempting to tamper when the timer 126 exceeds a predetermined amount of time allowed for the door 125a to be open. Additionally, the sensor 124, upon detecting tampering or attempting to tamper from the cap 120 via movement of the conductive tape 130, may send a signal to the controller 121 when the user breaks or attempts to break the cap 120, by applying some force to remove the cap 120, such as twisting or pulling the cap 120, but is not limited thereto. Alternatively, the sensor 124, upon detecting tampering or attempting to tamper from the main body 110 via the wire mesh 140, may send a signal to the controller 121 when the user breaks, attempts to break, melts via heat, or attempts to melt via heat the main body 110, but is not limited thereto. In the event the sensor 124 detects the user has tampered with or attempted to tamper with the main body 110 or the cap 120, the controller 121 may instruct the timer 126 to trigger the alarm by turning on the light 127. The light 127 may be a steady light or a flashing light. Furthermore, the controller 121 may send a signal to the external control unit 10 to alert a third party, such as a prescribing doctor, family, and police, that the user has tampered with or attempted to tamper with the main body 110 or the cap 120.

The biometric scanner 122 may be touched by the user's finger. As such, the biometric scanner 122 may send scanned biometric information to the controller 121 to check whether the scanned biometric information of the user is authorized based on biometric information data stored in the storage unit 121c. The user's authorization may be based on at least one of the stored biometric information of the user, an appropriate time of day, and a number of times the user has taken the medication. Prior to confirmation by the controller 121 that the user is authorized, based on the scanned biometric information, the manual slide 128 remains locked by the lock 128a and thus, the manual slide 128 cannot be moved. The manual slide 128 is considered in a closed position. Once the user has been confirmed by the controller 121 as being authorized, the lock 128a may be disengaged, allowing the user to pull the manual slide 128 to the open position and obtain access to the medication within the main body 110. In other words, the controller 121 may check the timer 126 to determine, based on the countdown, whether the user is currently authorized, when the user touches the biometric scanner 122. Subsequently, the user may invert the main body 110, such that it is now upside down to allow medication to fall through the funnel 129 via the funnel aperture 129a. Moreover, pulling the manual slide 128 may open the door 125a, allowing the medication to enter the medication receiving compartment 125 via the door 125a. Once the dosage has entered the medication receiving compartment 125, the door 125a closes to prevent further dosage from entering the medication receiving compartment 125. As the manual slide 128 and, consequently, the door 125a are now open, the timer 126 may begin the countdown. In order to stop the countdown, the user may push the manual slide 128 back in to the cap 120. As such, the manual slide 128 may contact the lock 128a, which relocks the manual slide 128 and prevents the manual slide 128 from being pulled until the user is subsequently authorized to retrieve another dosage of medication. Alternatively, after the medication has entered the medication receiving compartment 125, the door 125a may be immediately closed to prevent further retrieval of medication beyond what the user is authorized to receive. Specifically, the medication receiving compartment 125 may allow the user to retrieve an authorized dosage. Furthermore, the timer 126 may adjust the time of day to a later time to indicate the eligibility of the user to retrieve the next dosage of his/her medication.

Figure 2:
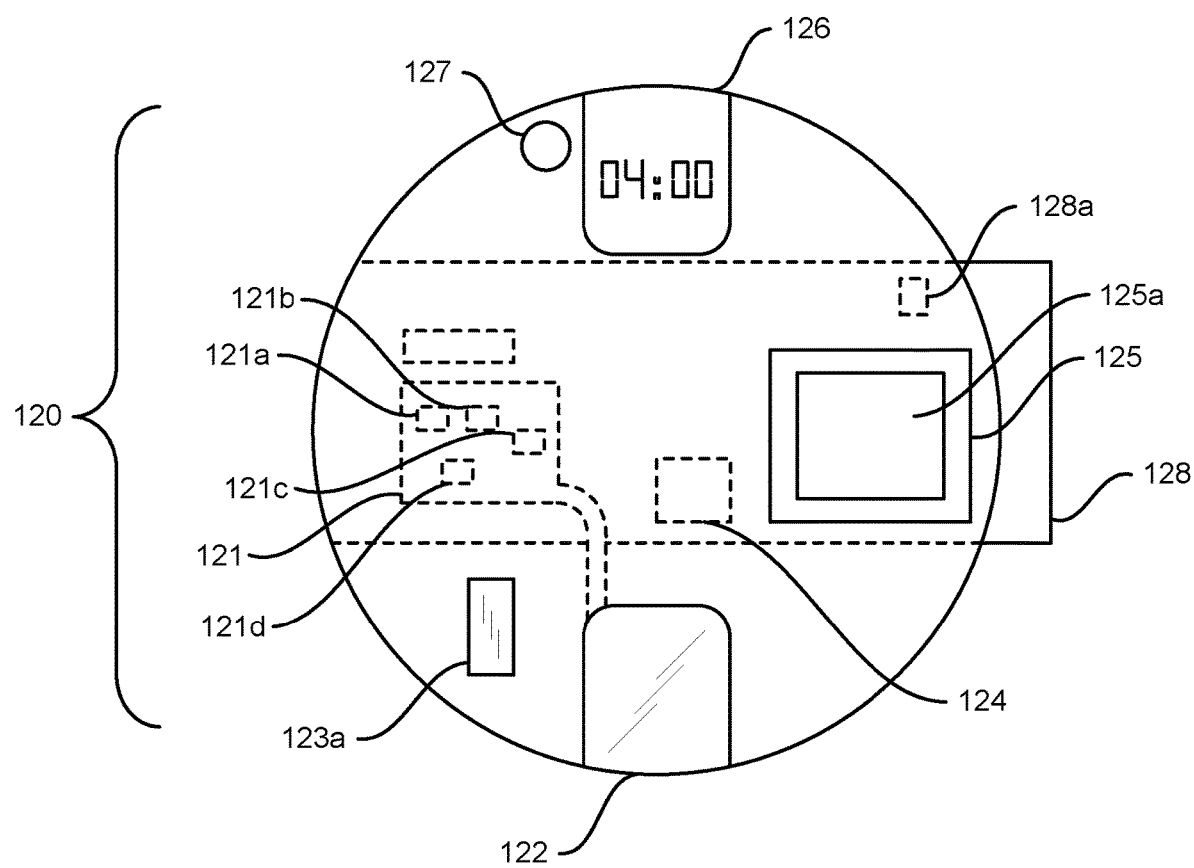
FIG. 2 illustrates a top view of the personalized medication dispenser, according to an exemplary embodiment of the present general inventive concept.

FIG. 2 illustrates a top view of the personalized medication dispenser 100, according to an exemplary embodiment of the present general inventive concept.

Referring to FIGS. 1 and 2, a personalized medication dispenser 100, includes the main body 110 to store medication therein, the main body 110 including a first end 111 having a base, and a second end 112 having an aperture 113 through which the medication is extracted, and the cap 120 to prevent the medication from being extracted from the aperture 113 of the second end 112, the cap 120 including the top portion 120a, including the biometric scanner 122 disposed on a surface of the top portion 120a to scan biometric information of the user, the controller 121 disposed within the top portion 120a to determine whether the biometric information is from the authorized user, and the medication receiving compartment 125 disposed within the top portion 120a to receive the medication in response to the determination that the scanned biometric information is from the authorized user, the bottom portion 120b to be at least partially inserted within the aperture 113 of the second end 112, and the manual slide 128 disposed between the top portion 120a and the bottom portion 120b to slide to an open position in response to the determination that the scanned biometric information is from the authorized user, such that the medication is received in the medication receiving compartment 125 when the manual slide 128 is in the open position.

Although a few embodiments of the present general inventive concept have been shown and described, it will be appreciated by those skilled in the art that changes may be made in these embodiments without departing from the principles and spirit of the general inventive concept, the scope of which is defined in the appended claims and their equivalents.

The invention claimed is:

1. A personalized medication dispenser, comprising:
a main body to store medication therein, the main body comprising:
a first end having a base, and
a second end having an aperture through which the medication is extracted; and
a cap to prevent the medication from being extracted from the aperture of the second end, the cap comprising:
a top portion, comprising:
a biometric scanner disposed on a surface of the top portion to scan biometric information of a user,
a controller disposed within the top portion to determine whether the biometric information is from an authorized user, and
a medication receiving compartment disposed within the top portion to receive the medication in response to the determination that the scanned biometric information is from the authorized user,
a sensor disposed within the top portion to detect the user has tampered with or attempted to tamper with at least one of the cap and the main body,
a timer disposed within the top portion having at least one of a clock, an alarm, and a countdown functionality,
a bottom portion to be at least partially inserted within the aperture of the second end, and
a manual slide disposed between the top portion and the bottom portion to slide to an open position in response to the determination that the scanned biometric information is from the authorized user, such that the medication is received in the medication receiving compartment when the manual slide is in the open position, such that the manual slide extends a distance across the cap, such that a length of the manual slide exceeds a diameter of the cap,
a conductive tape disposed within the main body such that the controller instructs the timer to alert a third party, when the sensor detects the user has tampered with or attempted to tamper with the cap,
a wire mesh disposed within the main body such that the controller instructs the timer to alert a third party, when the sensor detects the user has tampered with or attempted to tamper with the main body.

2. The personalized medication dispenser of claim 1, wherein the biometric scanner is at least one of a fingerprint scanner, an iris scanner, a facial scanner, and a voice scanner.

3. The personalized medication dispenser of claim 1, wherein the manual slide is unable to move prior to the determination that the scanned biometric information is from the authorized user.

4. The personalized medication dispenser of claim 1, wherein the top portion further comprises:
a light disposed within the top portion to turn on when the alarm is triggered.

5. The personalized medication dispenser of claim 4, wherein the controller instructs the timer to turn on the light when the sensor detects the user has tampered with or attempted to tamper with the cap.

6. The personalized medication dispenser of claim 4, wherein the controller instructs the timer to turn on the light when the sensor detects the user has tampered with or attempted to tamper with the cap.

7. The personalized medication dispenser of claim 1, wherein the controller instructs the timer to alert a third party that the manual slide has remained in the open position for a predetermined amount of time in response to the manual slide remaining in the open position for a predetermined amount of time.

8. The personalized medication dispenser of claim 7, wherein the third party is at least one of a prescribing doctor, family, and police.

9. A personalized medication dispenser, comprising:
a main body to store medication therein, the main body comprising:
a first end having a base, and
a second end having an aperture through which the medication is extracted; and
a cap to prevent the medication from being extracted from the main body, the cap comprising:
a top portion, comprising:
a biometric scanner disposed on a surface of the top portion to scan biometric information of a user,
a controller disposed within the top portion to determine whether the biometric information is from an authorized user, and
a medication receiving compartment disposed within the top portion to receive the medication in response to the determination that the scanned biometric information is from the authorized user,
a sensor disposed within the top portion to detect the user has tampered with or attempted to tamper with at least one of the cap and the main body,
a timer disposed within the top portion having at least one of a clock, an alarm, and a countdown functionality,
a conical bottom portion to be at least partially inserted within the aperture of the second end, and
a manual slide disposed between the top portion and the bottom portion to slide to an open position in response to the determination that the scanned biometric information is from the authorized user, such that the medication is received in the medication receiving compartment from a funnel aperture of the conical bottom portion when the manual slide is in the open position,
a conductive tape disposed within the main body such that the controller instructs the timer to alert a third party, when the sensor detects the user has tampered with or attempted to tamper with the cap,
a wire mesh disposed within the main body such that the controller instructs the timer to alert a third party, when the sensor detects the user has tampered with or attempted to tamper with the main body.

* * * * *